United States Patent [19]

Colucci et al.

[11] Patent Number: 5,554,509
[45] Date of Patent: Sep. 10, 1996

[54] NUCLEOTIDE PROBES AND METHODS FOR DETERMINING TAQI POLYMORPHISMS IN THE HUMAN APO(A) GENE

[75] Inventors: Giuseppe Colucci; Roberto Taramelli, both of Milan, Italy

[73] Assignee: Clonit SpA, Milan, Italy

[21] Appl. No.: 185,301

[22] Filed: Jan. 26, 1994

[30] Foreign Application Priority Data

Jan. 26, 1993 [GB] United Kingdom .................... 9301453

[51] Int. Cl.$^6$ ...................................................... C12Q 1/68
[52] U.S. Cl. ..................... 435/6; 935/77; 935/78
[58] Field of Search ................... 435/6, 91.2; 536/24.31, 536/24.33; 935/77, 78

[56] References Cited

FOREIGN PATENT DOCUMENTS

| | | |
|---|---|---|
| 0269260 | 6/1988 | European Pat. Off. . |
| 0414469 | 2/1991 | European Pat. Off. . |
| 0412557 | 2/1991 | European Pat. Off. . |
| WO90/05744 | 5/1990 | WIPO . |

OTHER PUBLICATIONS

Genomics, vol. 17, No. 1, Jul. 1993, H. G. Kraft, et al., "Demonstration of Physical Linkage Between The Promoter Region And The Polymorphic Kringle IV Domain In The Apo(a) Gene by Pulsed–Field Gel Electrophoresis", pp. 260–262.

Human Molecular Genetics, vol. 2, No. 7, Jul. 1993, Carolin Lackner, et al., "Molecular Definition of the Extreme Size Polymorphism in Apolipoprotein(a)", pp. 933–940.

Chemical Abstracts, vol. 114, No. 23, Jun. 10, 1991, AN 227059x, Hideaki Itoh, "Restriction Fragment Length Polymorphisms in Apolipoprotein Genes in Coronary Heart Disease and Diabetes Mellitus", p. 659.

The Journal of Clinical Investigation, vol. 85, No. 6, Jun. 1990, Angelo M. Scanu, et al., "Lipoprotein (a)", pp. 1709–1715.

M. D. Biggin, et al., "Buffer gradient gels and 35S label as an aid to rapid DNA sequence determination", Proc. Natl. Acad. Sci (USA) vol. 80, Jul. 1983, pp. 3963–3965.

J. W. McLean, et al, "cDNA sequence of human apolipoprotein(a) is homologous to plasminogen", Nature, vol. 300, Nov. 1987, pp. 132–137.

Lackner et al. J. Clin. Invest. 87: 2153–2161 (Jun. 1991).

Primary Examiner—Stephanie W. Zitomer
Attorney, Agent, or Firm—Oblon, Spivak, McClelland, Maier, & Neustadt, P.C.

[57] ABSTRACT

A polynucleotide probe capable of hybridizing to human genomic DNA between the TaqI sites immediately 5' and 3' of the polymorphic leader TaqI site of the human Apo(a) gene, said human genomic DNA being detectable by PCR amplification of the Apo(a) gene using the 5' and 3' primers:
5':5'CCT ATT TGG ATT TTG GAC GC 3'(SEQ ID NO. 1)
3':5'GAT AAC AGA CCA ATA GCT GT 3'. (SEQ ID NO. 2),
or a polynucleotide probe capable of hybridizing to human genomic DNA between the TaqI sites immediately 5' and 3' of the polymorphic kringle TaqI site of the human Apo(a) gene, said human genomic DNA being detectable by PCR amplification of the Apo(a) gene using the 5' and 3' primers:
5':5'CTG CAG ACA ACC CCT TAA ACA 3'(SEQ ID NO. 3)
3':5'GGA TCC TTA GAG ATA ACC TGC 3'(SEQ ID NO. 4).

The probes can be used for family studies or population studies to ascertain alleles associated with an increased risk of heart disease.

14 Claims, 1 Drawing Sheet

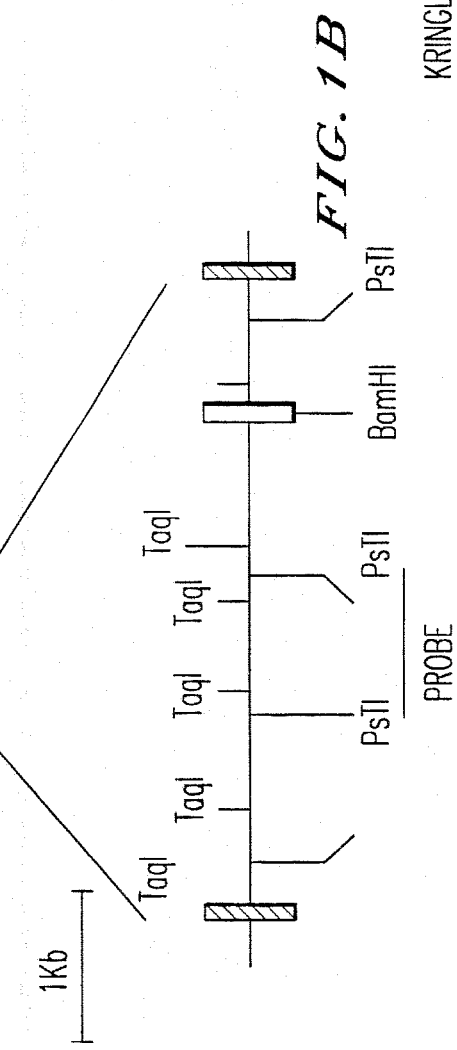
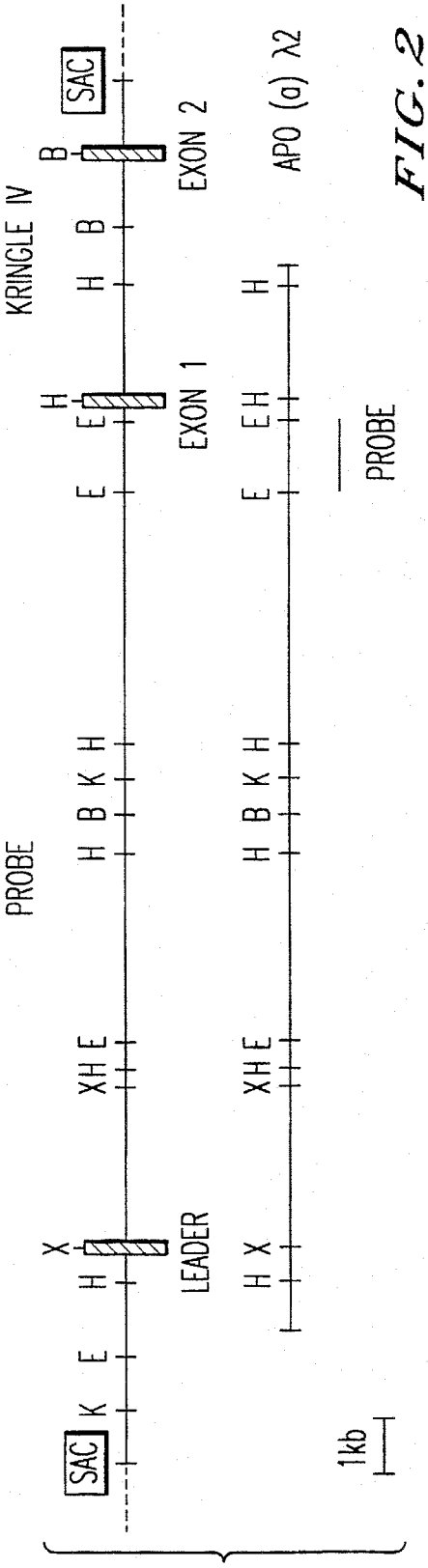
FIG. 1A
FIG. 1B
FIG. 2

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 1:

CCTATTTGGA TTTTGGACGC 20

( 2 ) INFORMATION FOR SEQ ID NO: 2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 2:

GATAACAGAC CAATAGCTGT 20

( 2 ) INFORMATION FOR SEQ ID NO: 3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 3:

CTGCAGACAA CCCCTTAAAC A 21

( 2 ) INFORMATION FOR SEQ ID NO: 4:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO: 4:

GGATCCTTAG AGATATCCTG C     21

( 2 ) INFORMATION FOR SEQ ID NO: 5:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO: 5:

TTTCTGTGGT CCTATTATGT TGA     23

( 2 ) INFORMATION FOR SEQ ID NO: 6:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO: 6:

CACCTGAGCA AAGCCATGT     19

NUCLEOTIDE PROBES AND METHODS FOR DETERMINING TAQI POLYMORPHISMS IN THE HUMAN APO(A) GENE

The present invention relates to polymorphisms within the apolipoprotein(a) gene, and the use of these polymorphisms in genetic studies.

In western countries heart disease ranks as one of the most common causes of morbidity and mortality in the adult population. Epidemiological studies have found multiple factors that correlate with an increased risk of coronary heart disease. Hypertension, cigarette smoking and hpyercholesterolemia are strongly associated with the incidence of coronary heart disease.

Several studies on the pathogenesis of atherosclerosis and its cardiovascular sequelae have pointed to the role of lipoproteins and their metabolites. Lipoproteins are macromelecular complexes of lipids and proteins which carry cholesterol and triglycerides from the intestine to the liver and other extrahepatic tissues.

There are four lipoprotein classes: chilomicrons, very low density lipoproteins (VLDL), low density lipoproteins (LDL) and high density lipoproteins (HDL). Each of these contains a protein subunit, the aproprotein, which includes eight major classes (apo A-I, A-IV, Apo B, Apo C-I, C-II, C-III, D and E).

Recently cDNA and in some cases genomic DNA have been obtained which served as probes to study the structure and organization of the aproprotein genes. These DNA probes, in combination with restriction fragment length polymorphism (RFLP) analysis, have led to the identification of haplotypes, individual RFLP profiles, which are associated with lipoprotein abnormalities and with an apparent risk of developing coronary heart disease. RFLPs are genetic variants which are identified as electrophoretic bands of different sizes for the presence or absence of cleavage sites for restriction enzymes.

RFLPs are a powerful genetic tool which allow the study of whether a genetic locus is involved in a clinical phenotype. There are basically two types of investigations. In one the frequency of an RFLP is compared in individuals with a clinical phenotype versus those without it. If a significant difference is observed, the allele identified by the RFLP is considered to be in association with the clinical phenotype. The RFLP may cause the phenotype or may be in linkage disequilibrium with the underlying mutation.

In the other type of study, individuals with a clinical phenotype are used as probands to identify large multigeneration families. The segregation of the clinical phenotype in family members is documented and RFLPs are used to distinguish which alleles at a given locus are present in each family member. The question is then asked whether the clinical phenotype is coinherited or linked to a particular allele in the family under study. Linkage implies that the gene for the disorder is in the vicinity of the gene which supplied the DNA probe. The allele linked to the phenotype is not expected to be the same in different families.

Using this approach, it was possible to detect RFLPs for Apo A-I and B-100 which were associated with an increased frequency of myocardial infarction and lipoprotein abnormalities.

Recent reports on an association between isoforms of apoprotein (a), a subunit of LDL, and myocardial infarction in hypcrololesterolemic patients has prompted us to study the gene of apo (a) to investigate the presence of RFLPs and their possible association with the incidence of coronary heart disease.

SUMMARY OF THE INVENTION

We have cloned several, overlapping portions of the Apo(a) gene from a YAC library of human liver DNA. DNA probes derived from these clones have been produced which can be used to study the organization of the gene and to search for RFLP in patients with coronary artery disease.

In our laboratory these probes have already detected and characterized several RFLPs in the general population.

Two of the RFLPs we have detected are TaqI polymorphisms within two regions of the Apo(a) gene. A TaqI polymorphism arises when a TaqI restriction endonuclease site is found to be present in some individuals but not in others. The TaqI site will be between two normally conserved TaqI sites immediately 5' and 3' of the polymorphic TaqI site. In the foregoing, "immediately" means the next TaqI site within the genome since of course the human genome will contain may thousands of such sites. The polymorphism can thus be viewed as follows:

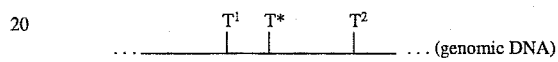

$T^*$ represents the polymorphic TaqI site in pan of the genomic DNA in an individual, and $T^1$ and $T^2$ are the conserved TaqI sites immediately 5' and 3' respectively. If an individual does not have the polymorphic TaqI site then cutting his DNA with TaqI will produce a DNA fragment from T1 to T2. If the cut DNA of the individual is separated by size, blotted and probed with a probe homologous to any part of the T1–T2 fragment, then a single band of DNA will be revealed. (This is described with reference to a single copy of genomic DNA although will hold true for an individual homozygous for this DNA region).

The exact nature of the probe does not matter to any great extent, as long as it will specifically detect any part of the T1–T2 region. In the description which follows, certain DNA probes which hybridize within particular T1–T2 regions are mentioned. It is not essential to use these particular probes; other probes can be derived from the same region of DNA. The suitability of the probes for use in detecting the T1–T2 region may be checked by reference to the probes described below; i.e., any candidate probe may be tested on DNA samples whose polymorphisms have been checked by a known probe, and the results obtained with the candidate probe and known probe compared to ensure that they are the same.

If an individual carries the T* site on either or both copies of the piece of genomic DNA being investigated, then two fragments of DNA will be obtained when the genomic DNA is cut with TaqI, ie. a T1-T* band and a T*-T2 band. If a probe homologous to the T1-T* band is used to examine the results of the digest, the T*-T2 band will not be detected. However, such a probe could be used in place of the T1-T* band, and could be derived in the manner described above.

In some cases, individuals without one or other of the sites T1 or T2 may exist. In a few of the cases, this may be due to large scale rearrangements of the genome, although in other cases it will be because T1 and/or T2 are themselves polymorphic, although only to a small extent. In such cases, this variation will be apparent when DNA from those individuals is analyzed although it will not generally prevent the determination of whether or not the T* site itself is present or absent.

DESCRIPTION OF THE DRAWINGS

FIG. 1 shows the region of the Apo(a) gene in the kringle IV repeat region. Part of the region has been expanded to indicate the polymorphic TaqI site and the immediate 5' and 3' TaqI sites. A PstI fragment which has been used as a probe is also indicated.

FIG. 2 shows the 5' region of the Apo(a) gene and indicates which part of this region was obtained in a single lambda phage clone. The leader is linked to the first Apo(a) kringle IV sequences in the clone. An EcoR1 fragment which may be used to detect the TaqI polymorphism described in this region is shown. Black boxes indicate the leader and kringle IV coding exons. Sac represents SacI cloning sites, K represents KpnI sites, E represents EcoRI sites, H represents HindIII sites, X represents Xbai sites and B represents BamI sites.

DETAILED DESCRIPTION OF THE INVENTION

The polymorphic TaqI site shown in FIG. 1A and 1B is referred to for the purposes of the invention as the "polymorphic kringle TaqI site".

The polymorphic TaqI site in the region shown in FIG. 2 is referred to for the purposes of the invention as the "polymorphic leader TaqI site".

The present invention thus provides a polynucleotide probe capable of hybridizing to human genomic DNA between the TaqI sites immediately 5' and 3' of the polymorphic leader TaqI site of the human Apo(a) gene, said human genomic DNA being detectable with a probe generated by PCR amplification of the Apo(a) gene using the 5' and 3' primers:

5': 5' CCT ATT TGG ATT TTG GAC GC 3' (SEQ ID NO. 1); and

3': 5' GAT AAC AGA CCA ATA GCT GT 3' (SEQ ID NO. 2).

The polynucleotide probe will usually be DNA although other polynucleotide probes, for example RNA or modified DNA or RNA probes may be used. The probe may carry a revealing label, for example $^{32}P$ or biotin.

By the term "capable of hybridizing" it is meant that the probe will hybridize to its target region of the Apo(a) gene under conditions of high stringency but not with other human genomic DNA. Preferably the probe will be exactly homologous to its target sequence although it will be appreciated that this will not always be necessary, as long as the probe can still selectively hybridize to its target DNA in the presence of other human DNA. For example, the probe may be about at least 75%, for example 80% or 90% homologous to its target region of DNA as long as this degree of homology will allow selective hybridization.

The probe may be an oligonucleotide probe, for example a probe of SEQ ID NO. 1 or SEQ ID NO. 2, or it may be a fragment of DNA, for example the EcoRI fragment defined by these oligonucleotides, ie. that of the Apo(a) gene which can be generated by PCR amplification of the Apo(a) gene with these oligonucleotides.

The probe may be any suitable size which provides the necessary specificity of hybridization. For example, an oligonucleotide probe may be from about 15 to 50, eg. 18 or 20 to 25 or 30 nucleotides in length. A probe derived from a restriction fragment may be for example from 50 base pairs to about 10 kb in size, eg from 200 to 1000 bp. A probe produced by a PCR of a selected piece of DNA may be any desired size capable of production by this method; 100 to 500 bp, e.g., 200 to 300 bp is typical.

The probe may be targeted to either the 5' side or 3' side of the polymorphic leader TaqI site, or it may span this site. When the probe is directed to one or other side of the site (and used to probe TaqI digested human DNA), the probe will reveal the 6.4 kb TaqI fragment present in individuals without the polymorphic leader TaqI site, and either the 1.4 kb or 5 kb fragments present in those individuals with the site. If the probe spans the polymorphic site in those individual with this site, it will reveal both the 1.4 and 5 kb fragments (assuming that the probe is of a sufficient size to hybridize to each side of the TaqI site).

The invention also provides a polynucleotide probe capable of hybridizing to human genomic DNA between the TaqI sites immediately 5' and 3' of the polymorphic kringle TaqI site of the human Apo(a) gene, said human genomic DNA being detectable by PCR amplification of the Apo(a) gene using the 5' and 3' primers:

5': 5' CTG CAG ACA ACC CCT TAA ACA 3'( SEQ ID NO. 3) and;

3': 5' GGA TCC TTA GAG ATA ACC TGC 3'(SEQ ID NO. 4).

The probes may be DNA, RNA, modified DNA or RNA probes as discussed above in connection with the polymorphic leader site, and these probes may also carry a revealing label. Suitable probes include those of SEQ ID NO. 3 and SEQ ID NO. 4 as well as the Pst1 fragment defined by these oligonucleotides.

The probe may be targeted to either the 5' side or 3' side of the polymorphic kringle TaqI site, or it may span this site. When the probe is directed to one or other side of the site (and used to probe TaqI digested human DNA), the probe will reveal the 1.6 kb TaqI fragment present in individuals without the polymorphic kringle TaqI site, and either the 1.3 kb or 0.3 kb fragments present in those individuals with the site. If the probe spans the polymorphic site in those individual with this site, it will reveal both the 1.3 and 0.3 kb fragments (assuming that the probe is of a sufficient size to hybridize to each side of the TaqI site).

The invention further provides a kit containing a pair of oligonucleotides of the sequence SEQ ID NO. 1 and 2 or of the sequence SEQ ID NO. 3 and 4. Such a kit may be used to generate a probe according to the invention using a PCR on a sample of DNA containing the Apo(a) gene or a fragment thereof containing the region of the gene to which the PCR primers bind.

In addition, the invention provides a probe or a kit as defined in any of the foregoing for use in a method of detecting TaqI polymorphisms within the human Apo(a) gene.

The probes and kits of the invention may be used to determine the TaqI polymorphism within the human Apo(a) gene in a sample of human DNA which comprises bringing the sample of human DNA into contact with a probe as defined above, and determining the TaqI polymorphism present in the sample.

The sample of DNA may be from any human tissue. It will often be convenient to obtain the sample from a sample of blood.

The probes according to the invention may be used for family studies. Thus, the invention provides a method for determining the parental origin of the Apo(a) genes of an individual which comprises bringing a sample of the individual's DNA into contact with a probe as defined in any one of claims 1 to 3 in order to determine the leader TaqI polymorphism or a probe as defined in any one of claims 4 to 6 in order to determine the kringle TaqI polymorphism present in the individual, and comparing the result obtained with the result(s) obtained when DNA from either or both biological parents is subjected to examination with a probe capable of detecting the same polymorphisms.

Desirably, the probe used to examine the individual's DNA will be the same probe as used to examine the parents DNA, although since the target region of the genome can be used to define different probes, it is not essential to use the same probe. It will be convenient to do so when the examination of the individuals and parent(s) DNA is conducted in a single experiment, for example on a single Southern blot.

In some family studies, it will often be desirable in order to determine the inheritance of particular Apo(a) alleles to examine DNA from one or more of the individual's biological grandparents or siblings.

Family studies can be especially useful to study the alleles of Apo(a) inherited in individuals where one or more of the individual's parents or grandparents has high blood levels of apolipoprotein (a) and/or a history of heart disease.

In order for studies of the above type to be informative, it may sometimes be necessary and in any event is usually desirable to analyze the sample or samples of DNA being examined with a second probe capable of detecting a different TaqI polymorphism within the Apo(a) gene. For example, if the DNA is examined with the kringle TaqI probe, then the individual may be further examined with the leader TaqI probe, or vice versa. Both probes may be used simultaneously because the TaqI polymorphic bands each detect are of different sizes. The probes of the invention may also be used with other probes for the Apo(a) gene or indeed with other probes for other genes. Such genes include other genes associated with lipoprotein or cholesterol metabolism.

The probes of the invention may also be used in population studies. It has been found in a variety of cases that certain alleles are associated within a population with the presence or absence of certain phenotypic traits. This phenomenon, well known in connection with for example certain human histocompatibility (HLA) genes, is known as linkage disequilibrium. The probes of the invention may be used to establish linkage disequilibrium between an allele of either or both of the polymorphic alleles of the invention and the risk of heart disease, eg an increased risk of heart disease.

The invention thus provides a method of assessing an individual member from a reference population for the risk of heart disease which comprises determining the leader TaqI and/or kringle TaqI polymorphisms of the Apo(a) gene in a sample of DNA from the individual, and assessing the risk of heart disease by reference to the estimated incidence of heart disease in the reference population of other individuals carrying the same Apo(a) leader TaqI and/or kringle TaqI polymorphisms.

In some cases, a linkage disequilibrium of a particular allele and a risk of disease may be found in certain ethnic populations but not in others. Thus, desirably the reference population is of the same ethnic origin as the individual when the risk of heart disease in that individual is assessed. For example, the population may be a Western European or North American Caucasian population, where the incidence of heart disease is relatively high compared to other populations.

The following examples illustrate the invention.

Example 1: Cloning of an Apo (a) Inter-Kringle Probe Detecting a Taq RFLP

A human cosmid library made with the vector pWE1S was purchased from Stratagene, La Jolla, Calif. and screened with a probe derived from the first Apo (a) Kringle IV which was obtained by gene amplification using the following oligonucleotides primers Mc Lean J. et al. Nature 300:132–239, 1987: upstream primer 5'-TTT CTG TGG TCC TAT TAT GTT GA-3'(SEQ ID NO. 5) downstream primer 5'-CAC CTG AGC AAA GCC ATG T-3'(SEQ ID NO. 6)

Gene amplification was carried out on genomic DNA for 32 cycles which included: denaturation 94° for 300 sec, annealing 55° for 60 sec, extension 92°, for 60 sec.

The cosmid library was plated on twenty Petri dishes (150 mm) with LB media containing 50 mg per liter of ampicillin. Dishes inoculated with approximately 40,000 colonies were incubated overnight at 37° C. Nitrocellulose filter lifts of the plates were prepared and hybridized with Kringle IV probe in 3×SSC/Denhardt at 65° C. overnight; washings were done in 0.3×SSC at 65° C. Positive recombinants were isolated as described by Maniatis T. et al. Molecular Cloning: a Laboratory Manual. Cold Spring Harbor Laboratory. Cold Spring Harbor, N.Y. 1989.

One of the positive recombinants was digested with several enzymes (Eco RI, Bgl II, Asp I, KpnI, TaqI) separately and in combination. Due to the particular repeated Kringle structure of the Apo (a) gene, the genomic Kringle unit was found to be contained in a repeated 5.5 Kb Eco RI and BgI fragments.

The recombinant cosmid contained approximately 7 of such repeats that could easily be excised by digestion with either Eco RI (E) or Bgl II (Bg) enzymes. One of the 5.5. Kb Bgl II Kringle containing fragments was subcloned into the Bgl II cut plasmid pGEM 7 (Promega) Madison, Wis. A restriction map of it is presented in FIG. 1. In order to demonstrate that the Kringle containing sequences were specific for Apo (a) and not derived from other related genes, sequence determination was performed with oligonucleotides derived from the Apo (a) cDNA Mc. Lean J. et al Nature 300:132–139, 1987. DNA analysis was carried out by dideoxynucleotide Chain Termination method according to Biggin M.D. et al. Proc. Natl. Acad. Sci USA 80:3963–3965, 1983 and the sequence data confirmed that the cosmid derived clone contained Apo (a) specific regions, perfectly matching the DNA sequence by Mc Lean J. et al. Nature 300:132–139, 1987 (see above).

From the intron between two Kringle IV a 1.2 Kb Pst I-PstI I probe was derived and was used to screen Southern Blots for detecting restriction length polymorphisms (RFLPs). Hybridization was carried out in 3×SSc/Denhardt at 65° overnight, post-hybridization washings in 0.3×SSC at 65°.

The enzyme Taq I resulted to be polymorphic with two alleles whose molecular weights are 1.6 and 1.3 Kb according to the presence/absence of one of the Taq I sites. From a population screening the frequency of the minor allele was 40% and the Mendelian inheritance of the polymorphism was documented in two informative families.

Example 2. Cloning of an Apo (a) Intron Probe Defining a Frequent RFLP.

Because of the expected large size of the human Apo (a) gene a YAC (Yeast Artificial Chromosome) library was screened by gene amplification with the same oligonucleotide pairs used in cloning the APO(a) inter-kringle probe (see above) Mc Lean J. et al. Nature 300: 132–139, 1987. Gene amplification was carried out on genomic DNA for 32 cycles which included: denaturation 94° for 300 sec, annealing 55° for 60 sec, extension 72° for 60 sec. The Screening was done at the Centre d'Etude du Polymorphisme Huamine (Paris). One positive recombinant was grown and DNA was extracted according to the procedure described by Little R. et al. Proc. Natl. Acad. Sci USA 86:1598–1602, 1989.

The YAC DNA was partially cut with Sau 3A and fractionated on a sucrose gradient as described by Maniatis T. et al. Molecular Cloning: a laboratory manual. Cold Spring Harbor laboratory, Cold spring Harbor, N.Y. 1989. Fraction ranging 15–20 kb in size were ligated to Lambda Fix vector (stratagene) digested with Xho I, packaging (Gigapack II-Stratagene) and plating was done according to the manufacturers conditions.

The Lambda Library was screened simultaneously with a probe spanning the Apo (a) leader domain Mc. Lean J. et al Nature 300:132–139, 1987 and a probe from the first Apo (a) Kringle IV Mc Lean J. et al. Nature 300:132–139, 1987. Several positives were obtained but only two of them hybridized to both. FIG. 2 shows the restriction map of one of them.

The intron sequences separating the leader from the first Apo (a) Kringle IV were cut with Eco RI and subcloned into pGEM 7 plasmid (Promega). A 1.1 kb Eco RI-Eco RI fragment (see FIG. 2) was hybridized to a Southern Blot cut with Taq I and revealed a restriction fragment length polymorphism. Polymorphic bands of 6.4 and 5 kb were detected with the following conditions:

Hybridization in 3×SSC/Denhardt at 65° overnight, washings in 0.3×SSC at 65°. A family study on one informative family showed that the polymorphism was inherited in a Mendelian manner.

We claim:

1. A method of determining a TaqI polymorphism within the human Apo(a) gene in a sample of human DNA, which comprises
    (a) digesting the sample of human DNA with restriction enzyme TaqI,
    (b) contacting the sample human DNA with a probe which hybridizes to human genomic DNA between the TaqI sites immediately 5' and 3' of the polymorphic leader TaqI site of the human Apo(a) gene, said human genomic DNA being detectable by PCR amplification of the Apo(a) gene using the 5' and 3' primers:
    5': 5' CCT ATT TGG ATT TTG GAC GC 3'(SEQ ID NO: 1)
    3': 5' GAT AAC AGA CCA ATA GCT GT 3'(SEQ ID NO: 2), and
    (c) determining the TaqI polymorphism present in the sample by observing the size(s) of the fragment(s) in the sample to which the probe binds.

2. A method according to claim 1 wherein the sample of human DNA is total genomic DNA obtained from a sample of blood.

3. A method of determining a TaqI polymorphism within the human Apo(a) gene in a sample of human DNA, which comprises
    (a) digesting the sample of human DNA with restriction enzyme TaqI,
    (b) contacting the sample of human DNA with a probe which hybridizes to human genomic DNA between the TaqI sites immediately 5' and 3' of the polymorphic kringle TaqI site of the human Apo(a) gene, said human genomic DNA being detectable by PCR amplification of the Apo(a) gene using the 5' and 3' primers:
    5': 5' CTG CAG ACA ACC CCT TAA ACA 3'(SEQ ID NO:3)
    3': 5' GGA TCC TTA GAG ATA ACC TGC 3'(SEQ ID NO:4), and
    (c) determining the TaqI polymorphism present in the sample by observing the size(s) of the DNA fragment(s) in the sample to which the probe binds.

4. A method according to claim 3 wherein the sample of human DNA is total genomic DNA obtained from a sample of blood.

5. A method for determining the parental origin of the Apo(a) genes of an individual, which comprises
    (a) digesting a sample of the individual's DNA with restriction enzyme TaqI,
    (b) contacting the sample of the individual's DNA with a probe which hybridizes to human genomic DNA between the TaqI sites immediately 5' and 3' of the polymorphic leader TaqI site of the human Apo(a) gene, said human genomic DNA being detectable by PCR amplification of the Apo(a) gene using the 5' and 3' primers:
    5': 5' CCT ATT TGG ATT TTG GAC GC 3'(SEQ ID NO:1)
    3': 5' GAT AAC AGA CCA ATA GCT GT 3'(SEQ ID NO:2),
    (c) determining the leader TaqI polymorphism present in the individual by observing the size(s) of the DNA fragment(s) in the sample to which the probe binds, and
    (d) comparing the result obtained with the result(s) obtained when DNA from either or both biological parents is subjected to steps (a), (b) and (c), thereby determining the parental origin of the Apo(a) genes of the individual.

6. A method according to claim 5 wherein the probes used to examine the individual's DNA and the parent(s) DNA are the same.

7. A method according to claim 5 wherein a sample of DNA from one or more of the individual's biological grandparents or siblings is also examined.

8. A method according to claim 5 wherein one or more of the individual's parents or grandparents has high blood levels of apolipoprotein (a) and/or a history of heart disease.

9. A method according to claim 5 which additionally comprises examining the sample or samples of DNA being examined with a second probe capable of detecting a different TaqI polymorphism within the Apo(a) gene.

10. A method for determining the parental origin of the Apo(a) genes of an individual, which comprises
   (a) digesting a sample of the individual's DNA with restriction enzyme TaqI,
   (b) contacting the sample of the individual's DNA with a probe which hybridizes to human genomic DNA between the TaqI sites immediately 5' and 3' of the polymorphic kringle TaqI site of the human Apo(a) gene, said human genomic DNA being detectable by PCR amplification of the Apo(a) gene using the 5' and 3' primers:
   5': 5' CTG CAG ACA ACC CCT TAA ACA 3' (SEQ ID NO:3)
   3': 5' GGA TCC TTA GAG ATA ACC TGC 3' (SEQ ID NO:4),
   (c) determining the kringle TaqI polymorphism present in the individual by observing the size(s) of the DNA fragment(s) in the sample to which the probe binds, and
   (d) comparing the result obtained with the result(s) obtained when DNA from either or both biological parents is subjected to steps (a), (b) and (c) thereby determining the parental origin of the Apo(a) genes of the individual.

11. A method according to claim 10 wherein the probes used to examine the individual's DNA and the parent(s) DNA are the same.

12. A method according to claim 10 wherein a sample of DNA from one or more of the individual's biological grandparents or siblings is also examined.

13. A method according to claim 10 wherein one or more of the individual's parents or grandparents has high blood levels of apolipoprotein (a) and/or a history of heart disease.

14. A method according to claim 10 which additionally comprises examining the sample or samples of DNA being examined with a second probe capable of detecting a different TaqI polymorphism within the Apo(a) gene.

* * * * *